(12) United States Patent
Smith et al.

(10) Patent No.: US 7,758,807 B2
(45) Date of Patent: Jul. 20, 2010

(54) MICROBIAL CONTROL WITH REDUCED CHLORINE

(75) Inventors: William L. Smith, Pleasanton, CA (US); Lachelle Arnt, Pleasanton, CA (US); Diane Mellett, San Francisco, CA (US)

(73) Assignee: The Clorox Company, Oakland, CA (US)

( * ) Notice: Subject to any disclaimer, the term of this patent is extended or adjusted under 35 U.S.C. 154(b) by 733 days.

(21) Appl. No.: 11/678,214

(22) Filed: Feb. 23, 2007

(65) Prior Publication Data

US 2007/0134127 A1    Jun. 14, 2007

Related U.S. Application Data

(63) Continuation-in-part of application No. 11/111,012, filed on Apr. 21, 2005, now abandoned, which is a continuation-in-part of application No. 10/828,571, filed on Apr. 20, 2004, now abandoned.

(51) Int. Cl.
```
A61L 9/00      (2006.01)
A62B 7/08      (2006.01)
A01M 13/00     (2006.01)
A61K 7/20      (2006.01)
A61K 7/36      (2006.01)
A61B 17/06     (2006.01)
B65D 25/08     (2006.01)
A61K 7/50      (2006.01)
A62D 3/00      (2007.01)
```

(52) U.S. Cl. ............. 422/37; 422/1; 422/5; 422/124; 43/124; 43/125; 424/53; 424/67; 424/76.1; 206/63.3; 206/219; 510/143; 252/187.23; 252/186.36

(58) Field of Classification Search .................. 422/1, 422/5, 37, 124; 43/124–125; 424/53, 67, 424/76.1; 206/63.3, 219; 510/143; 252/187.23, 252/186.36

See application file for complete search history.

(56) References Cited

U.S. PATENT DOCUMENTS

| | | | |
|---|---|---|---|
| 3,393,155 A |  | 7/1968 | Schutte et al. |
| 4,008,170 A |  | 2/1977 | Allan |
| 4,752,422 A |  | 6/1988 | Uchida et al. |
| 5,342,597 A |  | 8/1994 | Tunison, III |
| 5,820,822 A | * | 10/1998 | Kross .................. 422/37 |
| 6,363,734 B1 | * | 4/2002 | Aoyagi ................ 62/264 |
| 6,455,751 B1 |  | 9/2002 | Hoffman et al. |
| 6,528,014 B1 |  | 3/2003 | Parkhurst et al. |
| 6,602,466 B2 |  | 8/2003 | Hamilton et al. |

(Continued)

FOREIGN PATENT DOCUMENTS

GB    2329589    3/1999

(Continued)

*Primary Examiner*—Jill Warden
*Assistant Examiner*—Monzer R Chorbaji
(74) *Attorney, Agent, or Firm*—Alok Goel

(57) ABSTRACT

This invention relates to methods and apparatus for achieving microbiological control, especially using active sources that generate hypochlorous acid vapor with reduced levels of chlorine vapor. These methods are effective in confined spaces and sealed containers. The active sources may be contained within permeable containers and may be actively dispersed. The active sources may be in the form of solids, liquids or gels.

9 Claims, 2 Drawing Sheets

U.S. PATENT DOCUMENTS

| | | |
|---|---|---|
| 6,605,308 B2 | 8/2003 | Shane et al. |
| 6,607,696 B1 * | 8/2003 | Hamilton et al. .............. 422/37 |
| 6,673,137 B1 | 1/2004 | Wen |
| 6,716,885 B1 | 4/2004 | Twydell et al. |
| 6,767,509 B1 * | 7/2004 | Griesbach et al. ............. 422/29 |
| 6,936,220 B2 | 8/2005 | Hoshino et al. |
| 2002/0038768 A1 | 4/2002 | Kasuya |
| 2002/0176885 A1 | 11/2002 | Najafi et al. |
| 2002/0179884 A1 | 12/2002 | Hoshino et al. |
| 2003/0132279 A1 * | 7/2003 | Stemmle ...................... 232/31 |
| 2003/0138498 A1 | 7/2003 | Yoshikawa et al. |
| 2003/0156980 A1 | 8/2003 | Fischer et al. |
| 2003/0160209 A1 | 8/2003 | Hoffman et al. |
| 2003/0180385 A1 | 9/2003 | Martinelli et al. |
| 2004/0001777 A1 | 1/2004 | Hobson et al. |
| 2004/0146620 A1 | 7/2004 | Iwashita et al. |
| 2005/0214386 A1 | 9/2005 | Shaheen et al. |
| 2005/0216291 A1 | 9/2005 | Shaheen et al. |
| 2005/0221113 A1 | 10/2005 | Bitowft et al. |
| 2005/0232847 A1 | 10/2005 | Bromberg et al. |
| 2005/0232848 A1 | 10/2005 | Nguyen et al. |
| 2005/0233900 A1 | 10/2005 | Smith et al. |
| 2005/0235830 A1 | 10/2005 | Hughes |
| 2005/0265904 A1 | 12/2005 | Hardy et al. |
| 2005/0271559 A1 | 12/2005 | Ratcliff |
| 2007/0217946 A1 | 9/2007 | Smith et al. |
| 2008/0003171 A1 | 1/2008 | Smith et al. |
| 2009/0175958 A1 | 7/2009 | Shaheen et al. |

FOREIGN PATENT DOCUMENTS

| | | |
|---|---|---|
| JP | 20003-169842 | 3/1999 |
| JP | 2000-197689 | 7/2000 |
| WO | WO2004/045654 | 6/2004 |
| WO | WO2004/045655 | 6/2004 |
| WO | WO2007/008205 | 1/2007 |

* cited by examiner

MICROBIAL CONTROL WITH REDUCED CHLORINE

CROSS REFERENCE TO RELATED APPLICATIONS

The present application is a continuation-in-part of application Ser. No. 11/111,012 published as U.S. Pat. App. 2005/0233900, which was filed Apr. 21, 2005 now abandoned, entitled "Dry Delivery Hypochlorite", which is a continuation-in-part of application Ser. No. 10/828,571 published as U.S. Pat. App. 2005/0216,291, which was filed Apr. 20, 2004 now abandonded, entitled "Method for Diluting Hypochlorite", all of which are incorporated herein.

BACKGROUND OF THE INVENTION

1. Field of the Invention

This invention relates to methods and devices for delivering hypohalous acid vapor. The method and devices are useful for controlling microbiological contaminants and for treating the air, microbiologically contaminated surfaces, allergen containing surfaces, hard surfaces, food contact surfaces, hospital surfaces, food surfaces, kitchen surfaces, bathroom surfaces, human surfaces, animal surfaces, military equipment, transportation equipment, children's items, plant surfaces, seeds, outdoor surfaces, soft surfaces, air, wounds, and medical instruments.

2. Description of the Related Art

Consumers have many products to sanitize and disinfect their homes. The most common are spray cleaners and aerosol cleaners. These cleaners require frequent participation on part of the consumer and diligent application of these products to all areas where the removal of germs is desired. Examples of passive treatment exist based on the use of chlorine dioxide or chlorine gases to control microorganisms but these are in themselves potentially more hazardous, and their generators are also more hazardous than vapors from hypochlorite solutions or hypochlorous acid generators.

In one example of a passive treatment, PCT App. WO2004/045654 to Hamilton et al. describes the use of chlorine dioxide or ethylene gas to remediate mold in a bathroom, kitchen, restaurant, gym, medical facility, locker room, or aquatic facility. The method requires sealing off a room prior to exposing the mold to the gas by dispersing the gas in a gas dispersion device, such as a fogger, a spray bottle, an atomizer, or a humidifier.

U.S. Pat. App. 2004/0020007 to Lausevic describes a vacuum cleaner with a special attachment and a HEPA filter for removing mold. U.S. Pat. No. 6,440,365 to Poye et al. describes inspecting a building for *Stachybotris*, applying hydrochloric acid, and heating the applied treatment. U.S. Pat. No. 5,395,541 to Carpenter et al. describes an enzyme treatment to remove glycoside-containing microorganisms.

These technologies point out the difficulty in keeping indoor air and surfaces both safe and healthy. Based on the prior art examples, the need exists for a simple technology that can be used to remove germs from the indoor environment, while not requiring frequent and diligent effort.

SUMMARY OF THE INVENTION

In accordance with the above objects and those that will be mentioned and will become apparent below, one aspect of the present invention is a method for controlling a microbiological contaminant comprising the steps of: placing a composition that generates hypochlorous acid vapor and a reduced level of chlorine vapor into a confined space and exposing a microbiological contaminant to the composition.

In accordance with the above objects and those that will be mentioned and will become apparent below, another aspect of the present invention is an apparatus for controlling a microbiological contaminant comprising a permeable container and within the container a composition that generates hypochlorous acid vapor and a reduced level of chlorine vapor.

In accordance with the above objects and those that will be mentioned and will become apparent below, another aspect of the present invention is a treatment system comprising a non-permeable outer container; an object within the outer container bearing a microbiological contaminant; and an apparatus within the outer container for controlling a microbiological contaminant comprising a permeable container and within the permeable container a composition that generates hypochlorous acid vapor and a reduced level of chlorine vapor Further features and advantages of the present invention will become apparent to those of ordinary skill in the art in view of the detailed description of preferred embodiments below.

BRIEF DESCRIPTION OF THE DRAWINGS

The foregoing aspects and others will be readily appreciated by the skilled artisan from the following description of illustrative embodiments when read in conjunction with the accompanying drawings, wherein.

Figure 1:
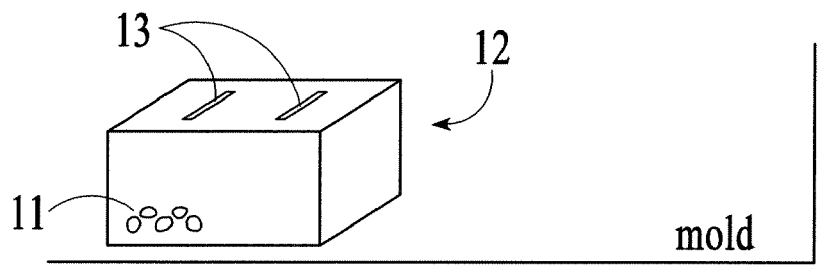
FIG. 1 illustrates one embodiment of the invention.

The invention is pointed out with particularity in the appended claims. The drawings are not necessarily to scale, emphasis instead generally being placed upon illustrating the principles of the invention. The advantages of the invention described herein, as well as further advantages of the invention, can be understood by references to the description taken in conjunction with the accompanying drawings.

DETAILED DESCRIPTION

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

As used herein and in the claims, the term "comprising" is inclusive or open-ended and does not exclude additional unrecited elements, compositional components, or method steps. Accordingly, the term "comprising" encompasses the more restrictive terms "consisting essentially of" and "consisting of".

It must be noted that, as used in this specification and the appended claims, the singular forms "a," "an" and "the" include plural referents unless the content clearly dictates otherwise. Thus, for example, reference to a "surfactant" includes two or more such surfactants.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage ("%'s") are in weight percent (based on 100% active) of the cleaning composition alone.

The term "surfactant", as used herein, is meant to mean and include a substance or compound that reduces surface tension when dissolved in water or water solutions, or that reduces interfacial tension between two liquids, or between a liquid and a solid. The term "surfactant" thus includes anionic, nonionic, cationic and/or amphoteric agents.

As used herein, the term "microbiological contaminants" refers to any microbial contaminant. Example of microbiological contaminants include, but are not limited to, fungi, bacteria, viruses, Protista, prions, archaea, and molds, including mold spores. Examples of such microbiological contaminants include *Stachybotrys Chartarum, Aspergillus niger, Absidia* sp., *Acrodorticm salmoneum, Aspergillus candies*, anthrax, etc.

The composition can be used to control microbiological contaminants. The composition can be used as a disinfectant, sanitizer, and/or sterilizer. As used herein, the term "disinfect" shall mean the elimination of many or all pathogenic microorganisms on surfaces with the exception of bacterial endospores. As used herein, the term "sanitize" shall mean the reduction of contaminants in the inanimate environment to levels considered safe according to public health ordinance, or that reduces the bacterial population by significant numbers where public health requirements have not been established. An at least 99% reduction in bacterial population within a 24 hour time period is deemed "significant." As used herein, the term "sterilize" shall mean the complete elimination or destruction of all forms of microbial life and which is authorized under the applicable regulatory laws to make legal claims as a "Sterilant" or to have sterilizing properties or qualities.

The term "surface" refers to hard and soft surfaces and includes, but are not limited to, tile grout, plaster, drywall, ceramic, cement, clay, bricks, stucco, plastic, wallpaper, fabric, tiles, cement, and vinyl flooring, heating and/or cooling fins, filters, vanes, baffles, vents, crevices in walls or ceilings, paper and wood products such as lumber, paper, and cardboard, woven products such as blankets, clothing, carpets, drapery and the like. The term surface also includes human surfaces, animal surfaces, military equipment, transportation equipment, children's items, plant surfaces, seeds, outdoor surfaces, soft surfaces, air, wounds, and medical instruments, and the like.

As used herein "pouch" refers to a hollow receptacle defining a volume. The pouch is "closed" in the sense that the actives are substantially retained within the pouch and the pouch volume is substantially sealed around its perimeter. However, the material or materials used to construct the pouch are chosen to allow exit of the gas generated. A pouch can be a sachet, an envelope or a receptacle defining an enclosed surface.

As used herein the term "sachet" means a closed receptacle for actives. The sachet is "closed" in the sense that the reactants are substantially retained within the sachet and the sachet volume is substantially sealed around its perimeter. However, the material or materials used to construct the sachet are chosen to allow exit of the gas generated. The material or materials used to construct sachets are referred to herein as "sachet layers." Sachet layers typically are constructed from a planar material, such as, but not limited to, a polymeric sheet or film. Preferred materials for sachet layers are described in greater detail below. Sachets can include more than one material, e.g. a sachet can comprise a barrier layer and sachet layer sealed about the perimeters of the layers to define a closed receptacle for actives. Another example of a sachet is a rigid frame defining one or more openings and one or more layers, including at least one sachet layer, disposed about the one or more openings to define a closed receptacle for actives.

"Permeable layer," as used herein, refers to a layer that permits passage of gas or vapor generated by an apparatus of the present invention. Permeable layers typically are constructed from polymeric materials. "Impermeable layer", as used herein, refers to a layer that substantially prevents or hinders passage of the generated gas or vapor. Impermeable layers can be constructed from various materials, including polymeric material, glass, metal, metallized polymeric material and/or coated papers. As used herein, barrier layers are impermeable layers. The skilled artisan will appreciate that what is considered to be an "impermeable layer" and what is considered to be a "permeable layer" is defined relative to the transmission rates of the respective layers used to construct apparatus of the present invention and the desired shelf life of the product. Relying upon the teachings disclosed herein, and the general knowledge in the art, the practitioner of ordinary skill will require only routine experimentation to identify and/or construct one or more impermeable layers and one or more permeable layers t adapted for the purpose at hand.

"Selective transmission films" are films that are neither perforated nor porous, but instead transfer gases through the polymer structure of the film. Selective transmission films can be multilayered or mixed polymer materials, where the layers and the polymers are chosen for controlled transmission of gases, such as carbon dioxide and oxygen. Selective transmission films are preferred in dry applications because they allow the gas to diffuse out of the apparatus. Further, such layers also can be employed to retain the initiating agent once released from a frangible pouch. Moreover, the selective transmission film can increase the stability of the apparatus prior to its use because it may not readily allow ambient water to diffuse into the apparatus, which could prematurely initiate the reactants.

As used herein "water vapor selective" refers to a material that selectively allows permeation of water vapor and substantially impedes permeation of liquid water. Suitably, the material excludes permeation of liquid water. Typically, the water vapor selective material is hydrophobic. The skilled practitioner typically refers to water vapor selective material as water impermeable, although water vapor can permeate the layer, and refers to materials that allow permeation of liquid water as water permeable. Suitable water vapor selective materials can be made from a variety of materials including, but not limited to, polytetrafluoroethylene (PTFE), polypropylene (PP), polyethylene (PE), and fluorinated ethylene propylene (FEP). Some water vapor selective materials are applied to a web that provides structural integrity to the material, e.g. where the material is thin and requires support to prevent tearing during manufacture and use.

Examples and embodiments of the materials and apparatuses described herein are also disclosed in U.S. Pat. Nos. 6,607,696 and 6,602,466, as well as PCT Publication No. WO 03/05146, all entitled "Methods and Apparatus for Controlled Release of a Gas," the entire disclosures of which are incorporated in their entirety by this reference.

Control of Microbiological Contaminants

In one aspect, the present invention provides a method for controlling a microbiological contaminant. The method generally includes the step of exposing a microbiological contaminant to a gas, e.g. hypochlorous acid, thereby controlling the microbiological contaminant. In one embodiment, the microbiological contaminant can be found in the air. In one embodiment, the microbiological contaminant can be found on a porous surface, such as tile grout, plaster, drywall, ceramic, cement, clay, bricks, stucco, caulking, heating, ventilating, and air conditioning (HVAC) system ducting, ductwork, insulation, and plastic. The microbiological contaminant can be found on a textured surface, such as wallpaper, fabric, tiles, cement, and vinyl flooring. The microbiological contaminant can also be found in other types of interstices or voids, including those defined by heating and/or cooling fins, filters, vanes, baffles, vents, crevices in walls or ceilings, paper and wood products such as lumber, paper, and cardboard, woven products such as blankets, clothing, carpets, drapery, insulation, ceiling tiles, floor coverings, HVAC system, ductwork, shoes, insulation and the like.

The microbiological contaminants can include a mold, mildew, a bacterium, a fungus and/or a virus, e.g. *Aspergillus niger, stachybotrys*, and penicillin digitatum. The control encompassed by the present invention can include cleaning, sanitizing, deodorizing, sterilizing, or killing target microbiological contaminants. This control can include killing a mold spore population and/or a mold population. The method can include controlling one or more microbiological contaminants in a bedroom, bathroom, kitchen, refrigerator, toy box, play area, storage area, restaurant, gym, medical facility, locker room, or aquatic facility. The present invention can be used for a variety of applications, including delivery of a gas to residential and commercial surfaces, and for a variety of purposes including, but not limited to disinfecting, deodorizing, bleaching, sanitizing, and sterilizing.

Forms

Figure 2:
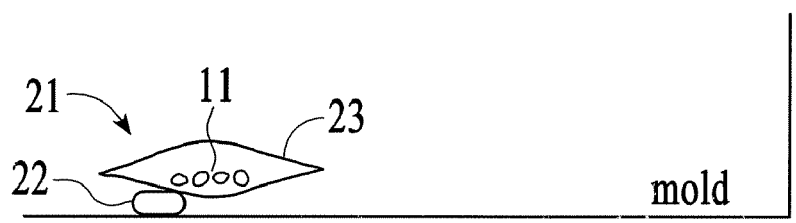
FIG. 2 illustrates another embodiment of the invention.
Figure 3:
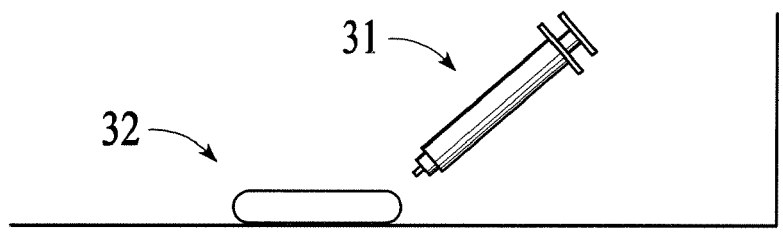
FIG. 3 illustrates another embodiment of the invention.
Figure 4:
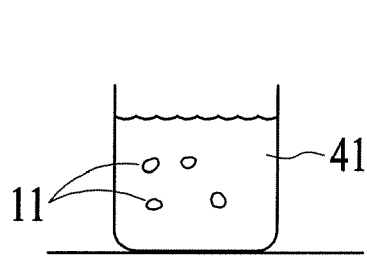
FIG. 4 illustrates another embodiment of the invention.
Figure 5:
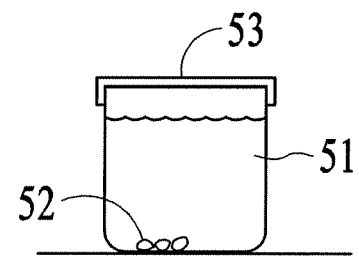
FIG. 5 illustrates another embodiment of the invention.

Aqueous solutions made from sodium hypochlorite emit sufficient amounts of hypochlorous acid vapor and possibly other available chlorine compounds (e.g. dichlorine monoxide and chlorine) to disinfect or prevent the growth of microorganisms on surfaces in contact with the vapor. As shown in FIG. 1, a liquid composition can be converted to a solid 11 to make it easier to contain the composition within a container 12 that emits the hypochlorous acid vapors through openings 13 to control mold or other microbiological contamination at a remote location. For example, the solution can be absorbed onto a mass of fibers or a porous solid such as puffed borax, fumed silica, or clay. Such solids may be free flowing or not depending on the ratio of liquid to absorbent. Free flowing solids can be made by mixing the aqueous solution with hydrophobic fumed silica. Hypochlorite solutions may also be encapsulated or microencapsulated using various shell-forming materials. In addition to the above containers, solids 11 or other forms can also be incorporated into pouches or sachets 21 made of woven or nonwoven materials, as shown in FIG. 2. Clays such as Laponite® can also be used to convert the liquid solution into a gel. Gels may be incorporated into any of the above containers or delivery systems. In addition, gels 32 may be applied to a surface using an applicator such as a syringe 31, as shown in FIG. 3. Solids may be sprinkled on a surface. These powders and gels will then emit the hypochlorous acid vapors into the space where microbial control is desired. Solutions may also be absorbed onto pads or nonwovens from which the vapors are emitted similar to some air fresheners. Solid carriers 11 may also be incorporated into wax gels 41, as shown in FIG. 4, from which the hypochlorous acid vapors are slowly emitted. In one embodiment, the gel includes volatile waxes such as cyclotetradecane. Solutions 51 may also be in equilibrium with solid hypochlorite releasing materials 52, as shown in FIG. 5, to prolong the life of the emitter. For example, dichlorohydantoins have a solubility limit that results in a sodium hypochlorite concentration of several hundred ppm. Excess dichlorohydantoin will remain as a solid that dissolves to replenish the hypochlorite as it is emitted as hypochlorous acid vapor.

Containers and Pouches

The vapor emitting composition may be a liquid, gel or solid in a container with one or more openings or perforations to allow the vapor to escape. Optionally, the opening may have a membrane or film 53 that is at least partially permeable to the hypochlorous acid vapor, as shown in FIG. 5. The composition, a liquid, gel or solid, may also be contained in a pouch made from a membrane or film that contains the composition but allows the vapors to pass. Generally, discrete amounts of actives disposed within a device such as a pouch, can control microbiological contaminants in a target area. The device can be affixed with an adhesive strip 22 (FIG. 2) or other fastening device to the surface to expose the microbial contaminants to the gas. In one embodiment, the active is substantially sealed in a pouch (e.g. a sachet) that includes a gas permeable layer. The gas permeable layer can be any permeable layer, e.g. a water vapor selective material or any of the permeable layers described herein. The sachet or pouch can wholly be constructed from gas permeable layers, or the gas permeable layer can comprise only a portion, e.g. one side 23 (FIG. 2) of a sachet. The remainder of the sachet or pouch can include impermeable materials or other materials, such as sachet layers forming an impermeable area. The device can also include additional elements such as additional sachets or one or more envelopes.

Suitable permeable and selective transmission films include 8181-G from Bemis® (OPET/adhesive/LLDPE), a film from American Packaging Corp. (PET/ink/adhesive/LLDPE), 24CTN from Exopack® (PET), a film from Alcan® (LLDPE), OW-134.5 from Pliant® Corp. (MDPE), GF-14 from Pliant® Corp. (LDPE), X5-202-315.2 from Pliant® Corp. (LLDPE/EVOH/m-PE), and GX-P from Pliant® Corp. (AlOx coated PE). Other suitable films include fluoropolymer films from W.L. Gore®.

The device can be in the form of a surface patch that generates a gas (e.g. hypochlorous acid), which diffuses across a permeable membrane (e. g. a water vapor selective layer), and migrates into the porous surface controlling the microbiological contaminant (e.g. mold and/or mold spores). In one embodiment, the patch includes an impermeable layer on the side of the apparatus to be placed opposite the surface to be treated. The utilization of an impermeable backing prevents the escape of the gas in the opposite direction, instead focusing diffusion to the surface containing the microbial contaminant.

The patch can also include an adhesive layer that faces the contaminated surface. The adhesive or other attachment means can be applied about the entire perimeter or only a portion of the perimeter. Other methods and devices for adhering an apparatus to a surface can also be employed, such as one or more clips, velcro, etc. In a suitable embodiment, the present invention features an apparatus for the generation of hypochlorous acid that is applied to dry wall. However, the present invention can be applied to any number of porous surfaces which may be found, but not limited to, the home, gym, dental and medical equipment, building restoration, food processing plants, and any other areas which would have a surface (e.g., a porous or textured surface), containing a contaminant. Further embodiments include apparatus in the form of a strip for application to selected surfaces and devices that include dispersion devices for application in larger areas, e.g. a room or a portion of a room.

The composition may be contained in a sachet or other porous form of containment that allows vapors such as hypochlorous acid to be released into the environment. The composition may also be adhered to a strip or some other device such as a double-sided adhesive tape for attachment inside containers such as trash cans, closets, drawers, diaper pails, etc. This allows the release of hypochlorus acid or other vapors that control odors, allergens and microorganisms in air or on surfaces. In a suitable embodiment, the apparatus includes an adhesive strip disposed about its perimeter, or a portion of its perimeter.

Figure 6:
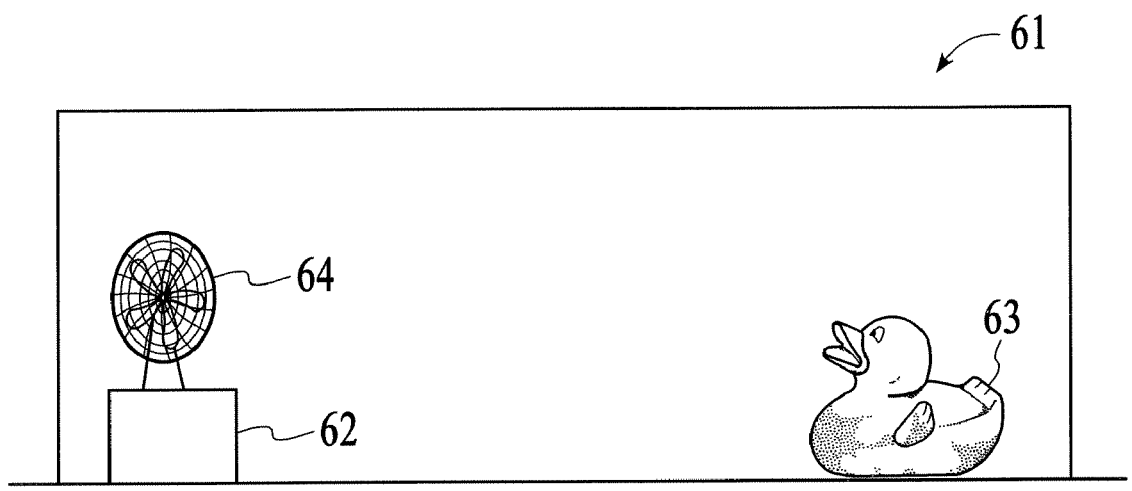
FIG. 6 illustrates another embodiment of the invention.

The source of hypochlorous acid vapor may be incorporated as part of an article or container that has a cavity and a door or lid into which items can be placed. Alternatively the source 62 of hypochlorous acid and the container 61 are separate entities which are combined at the time of use, as shown in FIG. 6. In either case, items, such as a toy duck, 63 are placed in the container 61 and the hypochlorous acid vapors either reduce the number of viable organisms on the item or they prevent the growth of microorganisms. This is accomplished without direct contact by the composition that emits the hypochlorous acid vapors. Thus, items such as electronic devices that are sensitive to immersion in water can be decontaminated. Multiple items can also be decontaminated at the same time. The decontamination of the items is done automatically by the vapors without wiping or scrubbing. The continuous nature of the hypochlorous vapor emission prevents the growth of microorganisms over time. This will prevent the growth of mildew and the development of odors in clothing and other items stored for a prolonged period. It will also preserve food and prolong food freshness in food storage containers. Articles which emit hypochlorous acid vapors may also be placed in various confined spaces such as drawers, closets, hampers, diaper pails, trash cans, toy boxes, and refrigerators. This will provide benefits to the contents of these confined spaces as discussed above.

Articles which emit hypochlorous acid vapors may also be used in rooms to disinfect surfaces or hinder the growth of microorganisms. They may be useful in showers to hinder the growth of mold and mildew or the growth of athelete's foot fungus. They may be placed near toilets to continuously disinfect surfaces such as the handle. This would also apply to other high touch areas such as door knobs. They may be used in doctor's offices to slowly disinfect environmental surfaces overnight with less effort than traditional disinfectants. The vapors may also be more effective at decontaminating difficult to reach places and irregular surfaces. The hypochlorous acid vapors can react with and neutralize many odorous compounds for odor control. These include compounds with sulfide, sulfhydryl, alkene, alkyne, aldehyde, ketone, amine, amide, nitrile and similar reactive groups, such as described in U.S. Pat. No. 6,749,805 for the deodorization of flatus.

The vapor emitting articles may be any form suitable to be hung using tape or hooks or they may be constructed to be set on a floor or other surface. They may have any shape and size. They may have mechanical louvers or vents to control the emission of the hypochlorous acid vapors or they may be placed inside containers with covers that screw or slide to form an opening of variable size.

Since the loss of hypochlorous acids during product distribution will affect the useful life of the product, it will be advantageous to have a product that is sealed during distribution and activated before use. This could be as simple as a tight fitting closure on a bottle or an overwrap of a barrier film on a pouch or sachet. The hypochlorous acid could be generated in situ by electrolysis. It can also be formed in-situ by altering pH. Alkaline hypochlorite solutions above about pH 11 are primarily composed of sodium hypochlorite which is not volatile. At the time of use the product could be activated by adding an acid to reduce the pH to where an effective amount of hypochlorous acid can be released. This could be done by adding a liquid or a powder to the solution or by removing or breaking a barrier that separates the two substances and allowing them to mix. An example is two compartments of a pouch or sachet that are separated by a film or valve that is broken or opened by applying pressure, vacuum, or some other physical means. Another approach would be to add water to a solid such as dichlorohydantoin, which results in at least partial hydrolysis of the solid to form a solution that contains hypochlorous acid.

Suitable Hypochlorous Acid Devices Substantially Free From Chlorine

Chlorine and chlorine dioxide vapors inhibit mold and kill bacteria, however, they also discolor dyes on fabrics and have relatively higher toxicity than hypochlorous acid, which makes chlorine dioxide and chlorine less desirable. Solutions that emit hypochlorous acid vapors can be modified to reduce or eliminate the co-emission of chlorine. Several approaches can be effective in mitigating the release of chlorine and chlorine dioxide and the discoloration of fabrics.

One approach is the reduction or elimination of water vapor, for example, using a desiccant. Chlorine does not absorb readily onto dry fabrics. The desiccant can be in a larger container that surrounds the container from which the hypochlorous acid vapors are emitted. The desiccant can also be sandwiched or otherwise contained within permeable or perforated plastic films that are used to cover the emitting container. Semi-permeable films, membranes or nonwovens that allow hypochlorous acid vapors to largely permeate, but restrict the release of water vapors may also be used (e.g. Gore-Tex®. films). The role of water can be demonstrated by comparing damage on dry fabric, fabric equilibrated at 80° F./80% relative humidity, and fabric soaking wet. The soaking wet fabric shows the worst dye damage.

Another approach is increasing the pH of the bleach solution to reduce chlorine. This is shown in Table 1 below. An isobaric line for constant hypochlorous acid vapor pressure can be calculated from literature values of various equilibrium constants for various concentrations of sodium hypochlorite and pH. Thus, one can maintain the performance of a desired concentration of hypochlorous acid but eliminate chlorine by increasing pH and hypochlorite concentration according to the isobaric line. This is just an example since other partial pressures of hypochlorous acid are also effective and may be more effective depending on the size of the container, etc. The higher bleach concentrations also allow for smaller volumes of solution since the volume of solution required to provide a certain number of moles of hypochlorous acid decreases as the concentration increases. These more concentrated solutions also maintain a more stable concentration with time because the amount of hypochlorous acid vapor emitted per hour is a much smaller fraction of the total amount of bleach than in a more dilute solution. This allows much longer product lifetimes for an emitter. For example, using 6000 ppm sodium hypochlorite at pH 9 provides continuous disinfection for more than a month in which contaminated slides are exposed and then evaluated every couple of days to confirm ongoing efficacy. In one embodiment, the sodium hypochlorite at about pH 9 is gelled using clay.

Another approach is minimizing the amount of vapor emitted. In this case the dose of vapor must be sufficient to kill microbes but not damage fabric dyes. In one embodiment, this can be done using a small volume of sodium hypochlorite solution at a dilute concentration at low pH. For example, 50 g of a 200 ppm sodium hypochlorite solution at pH 5.5 did not discolor fabrics in a 14 L container. However, essentially all the bleach was emitted from the solution in a relatively short period of time.

Another approach is using a filter to remove chlorine from the vapor leaving the emitter. Covering the emitter with nylon or with polyester fabric prevented the discoloration of fabric dyes. Unfortunately, the nylon also absorbed most of the hypochlorous acid as well and the vapor was not as effective at killing microorganisms. With polyester, the vapors were still an effective biocide and the vapor concentration (as measured electrochemically) was only partially reduced. Other polymers may also selectively remove chlorine from the vapor.

Another approach is using a fan 64 or spray to better disperse the vapors throughout the container 61, as shown in FIG. 6. There appears to be a non-linear concentration gradient of vapor as fabrics close to the emitter experience greater dye discoloration than those further away, but after some distance the fabric damage is essentially constant. This gradient was also confirmed by measuring the bleach absorbed into water at varying distances from the emitter. In addition, combinations of various approaches may also be effective.

Additional volatile agents may also be effective biocides. Examples include diacetyl, maltol, t-butyl hypochlorite, and hydrogen peroxide. With hydrogen peroxide vapors acceptable disinfection is achieved in closed containers with aqueous solutions that contain more than about 0.5% hydrogen peroxide, although the lower concentrations have some activity. Solid, nonvolatile compounds that contain an active halogen such as N-halohydantoins can also emit effective vapors by various means including equilibria with volatile chlorine containing species, hydrolysis with water vapor present in air, and autodecomposition. Such compounds can also be combined with solid acids or bases or other reactants to promote or regulate the formation of effective vapors.

Replaceable Cartridges

The device can have replaceable or disposable cartridges containing concentrated or dilute hypohalous acid in liquid or solid form that are readily placed in the device. The replaceable cartridges can also be generators of hypohalous acid, such as by electrolysis or hydrolysis. The replaceable cartridges can also deliver additional ingredients.

Portable Devices and Powered Devices

The device can contain an energy source, such as batteries, and can also contain a means for allowing recharging of rechargeable internal batteries via such means as a plug or port such that the consumer can conveniently recharge the batteries. Other means of providing energy sources that allow the device to be portable include methanol fuel cells or minerals that generate heat upon mixture with water, for example, mixing water with anhydrous calcium oxide. Portable devices would allow for disposable dispersion devices that could be taken for "on the go" occasions. For example, such systems could fit in the cup holders of vehicles.

In one embodiment of the device, the battery, fan, motor, and circuitry are designed to require a very low power draw, enabling the device to run continuously for a long period of time. Suitably, this embodiment of the device continuously draws less than 20 mA, or less than 10 mA, or less than 8 mA. To avoid the need for frequent battery replacement, the replaceable power supply of this embodiment preferably is designed to last at least one month, or at least two months, or at least three months, or at least four months.

Hypohalous Acid and Salts

Suitable hypohalous acids and salts may be provided by a variety of sources, including compositions that lead to the formation of positive halide ions and/or hypohalite ions; hypohalous acid, hypohalous acid salt, hypohalous acid generating species, hypohalous acid salt generating species; as well as compositions that are organic based sources of halides, such as chloroisocyanurates, haloamines, haloimines, haloimides and haloamides, or mixtures thereof. These compositions may also produce hypohalous acid or hypohalite species in situ. Suitable hypohalous acids and salts for use herein include the alkali metal and alkaline earth metal hypochlorites, hypobromites, hypoiodites, chlorinated trisodium phosphate dodecahydrates, potassium and sodium dichloroisocyanurates, potassium and sodium trichlorocyanurates, N-chloroimides, N-chloroamides, N-chlorosulfamide, N-chloroamines, chlorohydantoins such as dichlorodimethyl hydantoin and chlorobromo dimethylhydantoin, bromo-compounds corresponding to the chloro-compounds above, and compositions which generate the corresponding hypohalous acids, or mixtures thereof.

In one embodiment wherein the compositions herein are liquid, said hypohalite composition comprises an alkali metal and/or alkaline earth metal hypochlorite, or mixtures thereof. Compositions may comprise an alkali metal and/or alkaline earth metal hypochlorite selected from the group consisting of sodium hypochlorite, potassium hypochlorite, magnesium hypochlorite, lithium hypochlorite and calcium hypochlorite, and mixtures thereof.

The hypohalous acids and salt composition may be an equilibrium mixture of hypochlorous acid and sodium hypochlorite. The active species is present in an amount from above zero to about 15 weight percent of the composition, or from about 0.001 weight percent (10 ppm) to about 10 weight percent of the composition, or from about 0.005 (50 ppm) to about 5 weight percent of the composition.

The amount of available halogen oxidant in the composition is determined by placing samples of the composition into about 50 milliliters of distilled water, followed by addition of about 10 milliliters of a 10 weight/weight percent solution of potassium iodide and addition of about 10 milliliters of a 10 volume percent solution of sulfuric acid, the resulting mixture being well stirred. The resulting yellow to brown solution, whose color is the result of oxidation of free iodine ion ($I^-$) to molecular iodine ($I_2$), was then volumetrically titrated to an essentially colorless endpoint by addition of standardized 0.1 Molar sodium thiosulfate ($Na_2S_2O_3$) titrant. Calculation then expresses the result as percent of available molecular chlorine ($Cl_2$), that is to say assigning two equivalents per mole of titrated hypohalite oxidant. Stability results are then expressed by repeated assays over time using identically prepared samples resulting from the same composition, normalized to 100 percent representative of the starting available chlorine measured initially.

A very dilute solution (on the order of 40-80 ppm) of primarily hypochlorous acid can effectively deactivate allergens. Presumably the low levels of oxidant are still able to break up the allergen proteins, rendering them biologically inert. While still extremely effective, the low concentration and nearly neutral pH (6.9) composition of hypochlorous acid virtually eliminates surface damage. There is no sticky residue that can affect the feel of fabrics and there may be minimal dye damage. The solution may be aerosolized to treat air directly, or applied to surfaces.

Dilute hypohalous acid and salt technology is described in U.S. Pat. App. 2005/0214,386, U.S. Pat. App. 2005/0216,291, U.S. Pat. App. 2005/0232,847, U.S. Pat. App. 2005/0232,848, U.S. Pat. App. 2005/0221,113, U.S. Pat. App. 2005/0233,900 and U.S. patent application Ser. No. 11/277,642 entitled "Antimicrobial Product Combination", all of which are incorporated by reference herein.

Dry Forms of Hypohalous Acid

U.S. Pat. App. 2005/0233900 to Smith et al. describes a dry, powdered form of dilute hypochlorite and hypochlorous acid compositions suitable for use in the invention. Compositions can be prepared as described in U.S. Pat. App. 2003/0160209 to Hoffman et al., U.S. Pat. No. 6,716,885 to Twydell et al., U.S. Pat. No. 5,342,597 to Tunison, III, U.S. Pat. No. 3,393,155 to Schutte et al., and U.S. Pat. No. 4,008,170 to Allan, which are incorporated by reference herein. In accordance with one embodiment of the invention, solutions of dilute hypochlorite are coated using small quantities of treated (hydrophobic) particles by either vigorous agitation or by aerosolization of the solution in the presence of hydrophobic particles to form a solid powder. For example, when hydrophobic fumed silica particles, for example Cab-O-Sil TS-530®, are sheared in the presence of 100 ppm hypochlorite solution in approximately a 95:5-weight ratio of solution to silica, a dry powder can form. Also, a weight ratio of 80:20 can be utilized. The hydrophobic silica forms a porous coating of insoluble fine particles around the solution. Alternately, other colloidal particles or nanoparticles, such as alumina or clays, could be treated with a hydrophobic chemical to alter their surface characteristics and then used to encapsulate the hypochlorite solutions.

Fumed silica is formed by burning a volatile silicon compound. This forms primary particles of a few silicon oxide units with a size about 10 nm. These primary particles fuse together to form aggregates with a particle size on the order of 200 nm. These aggregates associate to form agglomerates that are bound by long-range intermolecular forces such as van der Waals forces. The agglomerates have typical particles sizes between 5 and 100 μm. In order to coat water droplets, about 50% or more of the surface silanol groups are typically blocked so they can not ionize, form hydrogen bonds, or otherwise interact with water. The most common approach is to react the silanol groups with silylating agents such as hexamethyldisilazane or polydimethylsiloxane. This converts the surface silanol groups into trimethylsilyl groups. Other agents that are commonly used to block surface silanol groups include trimethylchlorosilane, dimethyldichlorosilane, octamethylcyclotetrasiloxane, alkylsilanes (e.g. octylsilane and hexadecysilane), vinylsilanes (e.g. acrylsilane and methacrylsilane), and similar compounds. The surface silanol groups can also be blocked by association with organic cations or organic polycations (e.g. long chain alkyl amines, quaternary ammonium compounds, or carbamates); by association with polyvalent cations that are also ionically bound to organic ligands (e.g. aluminum stearate, chromium oleate, chromium methacrylate and other metal ions that are complexed to soaps or other anionic organic compounds); by esterification with alcohols or phenols (e.g. methanol, isopropanol, n-butanol, diazomethane, and many other similar compounds); and by association with various types of organic polymers (e.g. polymers formed on a silica surface using polyisocyanate and a polyol, using aldehydes, or using carbodiimides).

Generally, at least 50% of the surface silanol groups need to be blocked. However, decreasing the amount of unblocked surface silanol groups increases the maximum ionic strength and the maximum pH that can be tolerated. The pKa for treated fumed silica is unknown, but results for silica gel shows that as the surface silanol groups are partially neutralized, the pKa of the unneutralized groups increase. In other words, while the pKa of polymeric silica gel is about 6.5, as the silanol groups are neutralized the pKa of the remaining silanol groups approach the first dissociation constant for mono silicic acid (pH 9.8). With treated fumed silica, the pKa could be higher since the dissociation of the second, third, and fourth hydrogens of silicic acid have pKas of about 12-13. In all of these cases, increasing ionic strength would be expected to decrease the pKa and increase the ionization of unblocked silanol groups. Since data is not available for treated silicas, it has to be confirmed that pH and ionic strength have an impact on particle formation. Also, the critical values of pH and ionic below which particles can be formed with a specific type of treated fumed silica must be empirically determined.

Particles or powders of aqueous solutions coated by hydrophobic materials may be dry blended with various other dry or powdered materials. Separate particles containing incompatible ingredients can be mixed together. Said particles can be formed by coating separate solutions with hydrophobic silica. Other types of particles can be mixed with particles formed by coating solutions with hydrophobic silica. These other types of particles include ingredients that are coated with polymer shells that can be formed by a variety of techniques, including ingredients that are embedded in a matrix such as spray dried starch or sugar, co crystallized with another component such as sugar, absorbed onto a solid support such as fumed silica, zeolite, low density sodium carbonate, puffed borax, etc, or incorporated into polymer beads by absorption or during polymerization, etc. The other ingredients may also be used in solid forms such as powders, crystals, etc.

Ingredients that do not affect the wetting of treated fumed silica by water can be included in the solution that is being coated limited only by solubility and compatibility with other ingredients. Other ingredients such as surfactants and solvents that may affect the interaction of the treated silica and water may be added to the solution in amounts that do not interfere with the ability of the hydrophobic fumed silica to coat the water droplets. The tolerance for these interacting ingredients depends on the type of silylating agent used to treat the silica, the number of unblocked silanol groups, the nature of the ingredient, the ionic strength, and the pH of the solution.

Additional Actives

Additional actives that can be delivered include, for example, a surfactant, a perfume, a fragrance, an insect repellent, a fumigant, a disinfectant, a bactericide, an insecticide, a pesticide, a germicide, an acaricide, a sterilizer, a deodorizer, a fogging agent, and mixtures of these. These actives can be delivered with the hypohalous acid, in a separate vapor stream, or as separate vapors. Suitable fragrances for delivery are described in U.S. Pat. App. 2003/0024997 to Welch et al., which is incorporated herein.

Incompatible actives can be delivered by separating them from the hypohalous acid generator. Fragrances that are sensitive to oxidizing solutions can be added and dispersed into the atmosphere by using individual, replaceable cartridges that liberate the fragrance when heated. Other incompatible actives can be delivered in the same way.

Dispersion Devices

In order to speed the distribution of the hypochlorous acid vapors various mechanical dispersing devices such as fans 64 (FIG. 6), piezoelectric sprayers, and ultrasonic dispersers may be used. The life time of the hypochlorous acid emission may be controlled by the surface area through which vapors are emitted relative to the amount of liquid or solid that contains hypochlorous acid. In addition to aqueous solutions made from sodium hypochlorite, solid N-chloro compounds may also be used, since these may react with humidity or moisture to emit hypochlorous acid.

Figure 7:
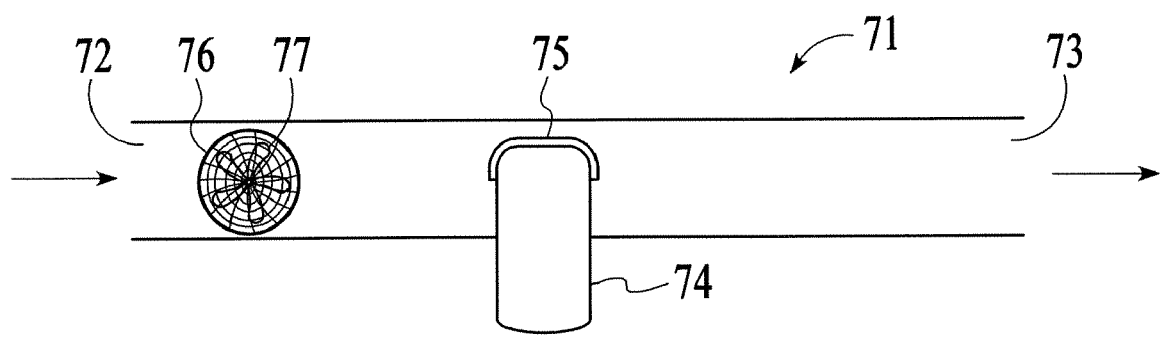
FIG. 7 illustrates another embodiment of the invention.

In one embodiment as shown in FIG. 7, the dispersion device is an air deodorizing device 71 having an air flow path from an air inlet 72 to an air outlet 73, and the deodorizing device 71 having a cartridge member 74 detachable from a portion of said deodorizing device 71, said cartridge member 74 comprising a filter member 75, wherein said cartridge member 74 is adapted to be arranged with respect to said portion of the deodorizing device such that said filter member 75 comes into contact with the air flowing along said air flow path of said deodorizing device 71; and an air moving member 76 for moving air along said air flow path, the air moving member 76 having a fan 77 connected to an electric motor (not shown) wherein said electric motor is powered by a source of electricity and wherein said air moving member is adapted to displace at least 10 ml or 100 ml of air per second through the air inlet of said deodorizing device.

Electrolytically Generated Hypohalous Acid

The device may be a self-generating plug-in or portable device, for example as described in U.S. Pat. App. 2003/0213704 to Scheper et al. and U.S. Pat. App. 2005/0067300 to Tremblay. The device may contain an electrochemical cell to generate dilute hypohalous acid. The electrochemical cells and/or electrolytic devices are those cells and/or devices that are self-powered and self-contained and which draw their electrical power from the unattached electrolytic device itself and/or alternatively from a building's electrical power supply to produce electrolyzed water. The device can be plugged in or can contain power to supply for the electrochemical cell, the power for any pumping means, the power for any propulsion means, the power for any indication or control means, and the like. The devices can comprise a housing that can be sealed or can be sealable to prevent electrolytic solution from entering the housing, except as intended. The body can have an inlet port, through which electrolytic solution can pass through to the electrochemical cell, contained therein.

In-situ generation of hypochlorous acid by electrolysis of slowly dissolving salt solution or brine may be a suitable source of hypochlorous acid when it is desired to emit hypochlorous acid vapor for a long period of time. The salt could be added using a stepping motor or screw type device, or the brine solution could be saturated and in equilibrium with excess salt to prolong the generation of hypochlorous acid. The salt could also be replenished in the electrolysis cell via osmosis using a membrane to separate an electrolysis cell with a more dilute salt concentration than in the larger reservoir. The electrolysis can be done using batteries or household current or rectified household current.

Another aspect of the invention is controlling the rate at which the emitter is exhausted so the article emits hypochlorous acid for a specific period of time. In some cases, the article will be designed to emit a high rate of flux to achieve a rapid reduction of microorganisms. This is achieved using a high concentration of hypochlorous acid (which may be formed in-situ) at a pH where a large percentage of the hypochlorite is in the form of hypochlorous acid. This could be used in a doctor's office as an overnight environmental surface sanitizer or disinfectant, elsewhere it would be acceptable to use all the hypochlorous acid in one use period. It may also include a fan or some other mechanical means to disperse the vapor. At the other extreme, a product could be designed to slowly emit hypochlorous acid over a long time to control microorganisms for a long period of time. Such articles could be useful to preserve items such as food or clothing during storage. In another aspect, the article is designed to achieve both initial fast and slowly continuous levels.

Spaces for Treatment

The present invention relates an apparatus or device and method for treatment of air, surfaces, and spaces. The apparatus and method for treatment can be suitable for use in various confined spaces, including, but not limited to, refrigerators, closets, clothes dressers, and the like. When the device is used for active treatment, it is possible to effectively use the device in even larger spaces, such as in a room, or closet. The apparatus and method of the present invention are, however, by no means limited to such uses. For example, it also possible for the device, or a portion thereof, to be used on its own for treating relatively small spaces like the inside of an automobile. The apparatus may also be provided with one or more components that can be used independently to treat the air, surfaces, spaces in other locations.

Confined spaces often have complex structures so that normal air convection does not reach every corner of the confined space. Such complex structures for example include separate compartments such as drawers or hollow elements inside the confined space. In accordance with one aspect of the method of the present invention, it is possible to also treat those portions of the confined space which are not sufficiently accessible to normal air convection. A confined space for which one aspect of the method of the present invention is particularly suitable comprises a compartment (e.g., the vegetable drawer in a refrigerator) which is within a confined space (the refrigerator) but which is separated from the remainder of the confined space (the interior of the refrigerator). With the method of the present invention it is therefore possible to treat all compartments in a confined space such as a refrigerator (which has enclosed compartments for vegetables, meats, etc.), a closet (which has shoe storage closets, clothes storage containers, etc.), or the like.

When used for treatment, the apparatus can provide several benefits, especially in confined spaces such as refrigerators, including, but not limited to: removing malodor from confined spaces; removing ethylene from confined spaces; maintaining the fresh odor of confined spaces; reducing the transfer of airborne bacteria in confined spaces; maintaining the freshness of food items; improving the quality of food items; maintaining the fresh taste of food items; preventing the transfer of odors between two food items; extending the useful life of food items; keeping food items fresh over a longer period of time; reducing spoilage of food items; reducing the incidence of freezer burn of food items in a freezer compartment; maintaining the fresh taste and/or odor of ice cubes (preferably ice cubes made by an automatic ice maker); increasing the cooling efficiency of a refrigerator; preventing or reducing the formation of ice crystals on ice cream in an opened or partially-sealed box stored in a freezer compartment; and combinations thereof. The present invention further relates to the use of the apparatus to achieve such benefits (i.e. technical effects).

Method of Use

The compositions may be used in personal care applications, including uses to treat wounds, rashes, acne, etc. Example of suitable uses include: sprinkling on wound before bandaging, treatment for urishol-induced rashes (e.g. poison ivy, poison oak), as a band-aid additive, as a wound cleaner and disinfectant, as a treatment for athlete's foot fungus, as a facial anti-acne defoliator, as a diaper rash preventer, as an acne facial wash powder, or suspended as particles in a cream or other carrier.

Other suitable personal care uses might include: a denture cleaner; a hand sanitizer/moisturizer, as a waterless hand sanitizer, as a anti-gingivitis toothpaste, as a tooth whitener including good for gums claim, as a foot powder deodorizer, as a mouth freshener, as a portable dry shower or deodorant, as a skin lightener for "age spots", as a hand sanitizer and moisturizer. Other potential uses include treating odors caused by bacteria and mildew, as a shoe cleaner, gym disinfecting powder, as a diaper pail odor remover, as a fridge deodorizer/freshener, as a sachet placed in food container, as sachet drawer fresheners, shoe powder deodorizer, as an air freshener for cars, as a garbage deodorizer, as a laundry dryer clothes freshener, as a garbage disposal freshener, for use anywhere baking soda is used, in a kitty litter box, as a freshener to carpets. Other potential uses include as a travel sanitizer, including camping gear, to treat cutting boards, as a powder to drop into air ducts to clean air, for waterless baby toy disinfecting, for closet mildew prevention, and as a seed treatment. Other potential uses include for water treatment, including as an additive for swimming pools, for cut flower freshness, for use in water filters for removal of microorganisms, and for direct addition to water. Other potential uses include use as a sprayable cleaning product, as a laundry detergent with bleach, to improve the odor control of an existing product, as a dry disinfecting wipe, in a direct bleach applicator device, as a dog/cat pet wash to treat odors, allergens, and as a disinfectant, as an upholstery cleaner to treat allergens, odors, germs, for waterless dish washing, as an additive to diapers to prevent odors or disinfect. Other potential uses include incorporation into items for long term use, for example in a sponge treatment so that sponge releases bleach with use, as an anti-mold building material additive, as an additive for grout and caulking, and as an additive to air filters for antimicrobial efficacy. Other potential uses include use to treat pests, for example as an ant preventer or for garden dusting. Other potential uses include industrial uses, including contaminated spill clean-up, algae removal from drinking water containers for farming, treating sick building syndrome, and as a general purpose disinfectant for hospitals. Other potential uses are in allergen deactivation (i.e. reaction of hypochlorous acid vapor to destroy proteins) and Weapon of Mass Destruction deactivation (e.g. hypochlorous acid vapor destroys many chemical weapons as well as microbial agents). Hypochlorous acid vapors can also deactivate many toxic gases such as cyanide, and hypochlorous acid vapor can also deactivate bacterial toxins—this could be useful where ever food is handled or served, could be useful for home canning—an alternate way to sterilize canning jars using hypochlorous acid vapors instead of boiling water, etc.

EXAMPLES

Table I represents calculated (estimated using literature equilibrium constants and thus only approximate) chlorine vapor for regular and low salt bleach at constant hypochlorous acid vapor concentration. This table shows that as the pH is raised, it takes a much greater concentration of hypochlorite to give the same hypochlorous acid concentration, but that the ratio of chlorine vapor to hypochlorous acid vapor is also much reduced, especially for low salt hypochlorite.

TABLE I

| NaOCl, mg/L | pH | HOCl vapor ppm | $Cl_2$ vapor ppm | $Cl_2$ vapor ppm Low salt |
|---|---|---|---|---|
| 200 | 5.5 | 5.377 | 0.944 | 0.236 |
| 204 | 6.0 | 5.377 | 0.304 | 0.076 |
| 216 | 6.5 | 5.377 | 0.102 | 0.026 |
| 256 | 7.0 | 5.377 | 0.038 | 0.010 |
| 313 | 7.3 | 5.377 | 0.023 | 0.006 |
| 380 | 7.5 | 5.377 | 0.018 | 0.004 |
| 427 | 7.6 | 5.377 | 0.016 | 0.004 |
| 487 | 7.7 | 5.377 | 0.014 | 0.004 |
| 522 | 7.75 | 5.377 | 0.014 | 0.003 |
| 561 | 7.8 | 5.377 | 0.013 | 0.003 |
| 655 | 7.9 | 5.377 | 0.012 | 0.003 |
| 774 | 8.0 | 5.377 | 0.012 | 0.003 |
| 923 | 8.1 | 5.377 | 0.011 | 0.003 |
| 1110 | 8.2 | 5.377 | 0.010 | 0.003 |
| 1347 | 8.3 | 5.377 | 0.010 | 0.003 |
| 1644 | 8.4 | 5.377 | 0.010 | 0.002 |
| 2018 | 8.5 | 5.377 | 0.010 | 0.002 |
| 2490 | 8.6 | 5.377 | 0.009 | 0.002 |
| 3083 | 8.7 | 5.377 | 0.009 | 0.002 |
| 3830 | 8.8 | 5.377 | 0.009 | 0.002 |
| 4770 | 8.9 | 5.377 | 0.009 | 0.002 |
| 5954 | 9.0 | 5.377 | 0.009 | 0.002 |
| 7445 | 9.1 | 5.377 | 0.009 | 0.002 |
| 9321 | 9.2 | 5.377 | 0.009 | 0.002 |
| 11683 | 9.3 | 5.377 | 0.009 | 0.002 |
| 14657 | 9.4 | 5.377 | 0.009 | 0.002 |
| 18400 | 9.5 | 5.377 | 0.009 | 0.002 |

Experiments have been done to determine the parameters that determine the rate of hypochlorous acid loss from solution. This was done spectrophotometrically and by titration. The mass of hypochlorous acid emitted is governed by pH, concentration, quantity of solution, the height of the solution and the amount of unobstructed surface area.

The presence of hypochlorous acid can be detected by moist starch-iodide indicator paper or by moist available chlorine indicator strips. Electrochemical analyzers that measure available chlorine can be used to measure the concentration of bleach vapors as if they were chlorine. These have been used to demonstrate the presence of hypochlorous in spaces some distance from the emitting solution. The decolorization of dye solutions by the emitted hypochlorous acid has also been followed as a function of time spectrophotometrically.

Hypochlorous acid vapors prevent the growth of mold and kill bacteria that have been deposited onto surfaces, for example in closed containers with volumes between 3 and 132 liters. Bacteria on surfaces behind other objects and not in a direct contact or line of sight, such as behind stuffed toys were killed despite the obstacle of the stuffed toy. Experiments in a 6×6×6 foot chamber demonstrate the inhibition of mold growth. Additional experiments also show that hypochlorous acid vapors can prolong the freshness of fruits and vegetables during refrigerated storage. In a closed container, the vapors may absorb on the surface of the container and provide a residual disinfecting benefit after the hypochlorous acid vapor emitter is removed and the container is reclosed.

In one example, 500 g or 1000 g of 206 ppm hypochlorite bleach at pH 5.52 was put in closed 69 L containers over 12 hours. Glass slides and fabric swatches inoculated with *S. aureus* were placed 30 cm from the bleach source. The inoculated samples were removed after 12 hours and the there was a 6 log reduction in organisms on both the glass slides and the fabric swatches. In another experiment in a 39 L container, 15 g of 219 ppm hypochlorite was placed in front of a continuous fan and 61 cm away from a polystyrene slide inoculated with *S. aureus*. After 24 hours, there was a 5 log reduction in organisms. In another experiment, the effectiveness of Gore-Tex® film in reducing water vapor and hypochlorous acid vapor loss was measured. Samples of 200 g of 1061 ppm hypchlorite bleach at pH 6.0 were placed in 14 L containers for 6 hours. One sample covered with Gore-Tex® lost 0.08% water and 1.8% of the hypochlorite. The other uncovered sample lost 0.11% water and 10.6% of the hypochlorite. Samples containing 200 ppm hypochlorite at pH 5.5 were covered with polyester or nylon fabric. These samples showed significantly reduced dye damage on fabric swatches containing bleach sensitive dyes that were placed 16 cm from the hypochlorite samples.

In another experiment, a 75 gm and a 150 gm open container of 6000 ppm hypochlorite at pH 9.0 were tested in separate 132 L enclosures with inoculated glass slides, inoculated fabric, and fabric with bleach sensitive dye placed 32 cm away. After 24 hours, the 75 gm container lost 352 ppm of hypochlorite and the 150 gm container lost 650.7 ppm of hypochlorite. The inoculated glass slide and inoculated fabric in both enclosures showed complete kill. The fabric damage in both enclosures was greatly reduced compared to experiments with pH 5.5 hypochlorite.

Disinfection testing and dye decolorization experiments show that hypochlorous acid vapors released from solutions, solutions absorbed onto fumed silica beads, and solution droplets coated with hydrophobic fumed silica are equally effective, as well as vapors are emitted from gels made using clay thickeners (Laponite®). These gels may be ringing gels that do not flow or spill. Indicator strips show that hypochlorous acid is emitted from solutions heat-sealed into Tyvec® (HDPE) pouches or sealed inside zipper storage bags made of polyethylene. The vapors pass through the polymer film, while the solution remains inside and the outer surface of the pouch remains dry.

Prototypes have been made by putting hypochlorous acid solutions into jars or bottles, heat-sealing such solutions into polyethylene pouches, and enclosing the powder made by mixing the solution with hydrophobic fumed silica into pouches made from nonwoven materials. Delivery devices have also been made by placing a film over a glass jar and holding the film in place with a screw closure ring. Some of the pouches or sachets were equipped with hangers or double sided tape. A prototype was also prepared in which a vial of solution with a wick was attached to a battery operated peizoelectric device that dispenses puffs of mist and vapor. A prototype was prepared by placing an open jar under a battery operated fan in a container that included slits to allow the air to enter from the room and air with hypochlorous acid vapor to be discharged into the room. Other prototypes have been contemplated as described herein. These include a device with a tray of solution under a blower and a device with a reservoir of liquid that is slowly flowed onto an ultrasonic horn to emit fine droplets of solution and vapor.

While various patents have been incorporated herein by reference, to the extent there is any inconsistency between incorporated material and that of the written specification, the written specification shall control. In addition, while the invention has been described in detail with respect to specific embodiments thereof, it will be apparent to those skilled in the art that various alterations, modifications and other changes may be made to the invention without departing from the spirit and scope of the present invention. It is therefore intended that the claims cover all such modifications, alterations and other changes encompassed by the appended claims.

We claim:

1. A method for controlling a microbiological contaminant comprising the steps of: placing a composition that generates hypochlorous acid vapor in which the chlorine concentration is reduced to less than 1% of the hypochlorous acid concentration into a confined space, and exposing a microbiological contaminant to the composition.

2. The method of claim 1, wherein the chlorine concentration is reduced to less than 0.2% of the hypochlorous acid concentration.

3. The method of claim 1, wherein the chlorine concentration is reduced by means of a desiccant.

4. The method of claim 1, wherein the chlorine concentration is reduced by means of a membrane that reduces chlorine permeability.

5. The method of claim 1, wherein the chlorine concentration is reduced by means of a hypochlorite composition between pH 8 and pH 10.

6. The method of claim 1, wherein the chlorine concentration is reduced by means of a hypochlorite composition below 300 ppm.

7. The method of claim 1, wherein the chlorine concentration is reduced by means of a filter that captures chlorine.

8. The method of claim 1, wherein the chlorine concentration is reduced by means of mechanical dispersion of the vapor.

9. The method of claim 1, wherein the chlorine concentration is reduced by means of a hypochlorite composition with low salt.

* * * * *